(12) United States Patent
Day

(10) Patent No.: US 6,508,864 B2
(45) Date of Patent: Jan. 21, 2003

(54) SEPARATION AND COLLECTION OF ANALYTE MATERIALS

(75) Inventor: Peter John Day, St. Albans (GB)

(73) Assignee: Graseby Dynamics Limited, Herts (GB)

( * ) Notice: Subject to any disclaimer, the term of this patent is extended or adjusted under 35 U.S.C. 154(b) by 0 days.

(21) Appl. No.: 10/004,003

(22) Filed: Nov. 14, 2001

(65) Prior Publication Data

US 2002/0078826 A1 Jun. 27, 2002

Related U.S. Application Data

(63) Continuation of application No. PCT/GB00/01853, filed on May 15, 2000.

(30) Foreign Application Priority Data

May 15, 1999 (GB) ............................................. 9911336

(51) Int. Cl.[7] ............................................... B01D 47/00
(52) U.S. Cl. .............................. 95/219; 96/316; 96/321
(58) Field of Search ..................... 95/216, 219; 96/301, 96/308, 316, 321

(56) References Cited

U.S. PATENT DOCUMENTS

| | | | |
|---|---|---|---|
| 1,888,603 A | * | 11/1932 | Mauthe |
| 2,578,315 A | * | 12/1951 | Parker |
| 3,990,870 A | * | 11/1976 | Miczek |
| 4,279,627 A | * | 7/1981 | Paul et al. |
| 4,948,396 A | * | 8/1990 | Barnes et al. |

FOREIGN PATENT DOCUMENTS

| | | |
|---|---|---|
| EP | 0244523 | 11/1987 |
| EP | 0473566 | 3/1992 |
| GB | 1177176 | 1/1970 |
| GB | 1500117 | 2/1978 |
| GB | 2284165 | 5/1995 |

* cited by examiner

Primary Examiner—Duane S. Smith
(74) Attorney, Agent, or Firm—Wallenstein & Wagner, Ltd.

(57) ABSTRACT

A cyclone separator, for the separation of particulate materials from a particle-bearing gas or vapour, in which the particle-bearing gas or vapour is injected into a separating chamber (10), and the particles centrifuged to a separating chamber wall (12) of the separating chamber (10) for collection, the separating chamber wall (12) being wetted by a liquid to assist in collection of the centrifuged particles from the separating chamber wall (12), the separating chamber wall being at least partly porous, the separating chamber wall (12) being wetted by the passage of the liquid through the porous part, to provide a more uniform wetting of the separating chamber wall (12), and hence more efficient particulate collection than previously achieved by prior art methods. The cyclone separator of the invention may also be used for the separation and collection of gas or vapour-borne vapours, in place of particulates.

22 Claims, 2 Drawing Sheets

SEPARATION AND COLLECTION OF ANALYTE MATERIALS

This Application is a continuation of International Application No. PCT/GB00/01853, with an international filing date of May 15, 2000, now pending (which is hereby incorporated by reference).

TECHNICAL FIELD

The present invention relates to cyclone separators such as are used to separate and collect, for analysis, gas- or vapour-borne materials, most usually in the form of particles.

BACKGROUND OF THE INVENTION

The principle of operation of such a cyclone separator involves the particle-bearing gas or vapour, typically air, being forced tangentially by means of a pressure differential into a cylindrical chamber. The particles, due to their mass are centrifuged to the wall of the chamber and are collected as they fall to the bottom of the chamber, the exhaust air being ducted away from the chamber through an exhaust port.

In one variant of the cyclone separator, a liquid, typically water, is sprayed into the particle carrying inlet air stream, usually just outside the collection chamber. The water droplets are centrifuged with the particles, and wash the collected particles to the bottom of the chamber from where the resulting solution or suspension can be pumped away for use or analysis. This variant is commonly referred to as a "wetted-wall" cyclone.

The wetted-wall cyclone may also be used for the collection of analyte material present in the incoming air in the form of air-borne vapours.

The known wetted-wall cyclone, operating with an inlet spray has a functional inefficiency in that, as a result of surface tension effects, the water impacting the wall of the cylone forms clumps and streams rather than a uniformly wetted surface, meaning that the wall washing is invariably of a inconsistent nature and the separation achieved is of variable efficiency.

It is thus one object of the present invention to provide an improved construction of wetted-wall cylone separator.

SUMMARY OF THE INVENTION

According to one aspect of the invention a wetted wall cyclone separator is provided with means enabling the inner surface of the wall of the separation chamber to be more uniformly wetted than possible with an inlet spray arrangement, thereby providing a more consistent and more efficient collection of materials introduced into the chamber in the incoming gas or vapour stream than hitherto.

In a preferred embodiment of the invention, the separation chamber has a wall comprised at least in part of a porous material through which a liquid may be forced to provide the more uniform wetting of the inner surface of the cylinder required to achieve the improved consistency and efficiency of sample collection.

The porous material may be a sintered material, for example a ceramic, or a metal, such as sintered stainless steel.

From another aspect the invention consists in a method of separation of a gas or vapour borne material by means of a cyclone separator in which the inner wall of the separator is wetted, and material incoming is collected and carried away by liquid flow across the wall, and in which the liquid is introduced into the separator so as to flow uniformly across the separator wall, thereby to improve the consistency and efficiency of separation.

The liquid may be introduced under pressure through the separator wall, by providing that the wall is at least in part porous.

From a still further aspect the invention consists in an instrument for separating, collecting and analysing gas or vapour borne materials, such instrument comprising a wetted wall cyclone separator in accordance with the present invention.

BRIEF DESCRIPTION OF THE DRAWINGS

Other aspects of the invention will be apparent from the following description of a cyclone separator in accordance with the invention, and an instrument incorporating such a cyclone separator, which are described with reference to the accompanying informal drawings of which.

DETAILED DESCRIPTION OF THE PREFERRED EMBODIMENTS

Figure 1:
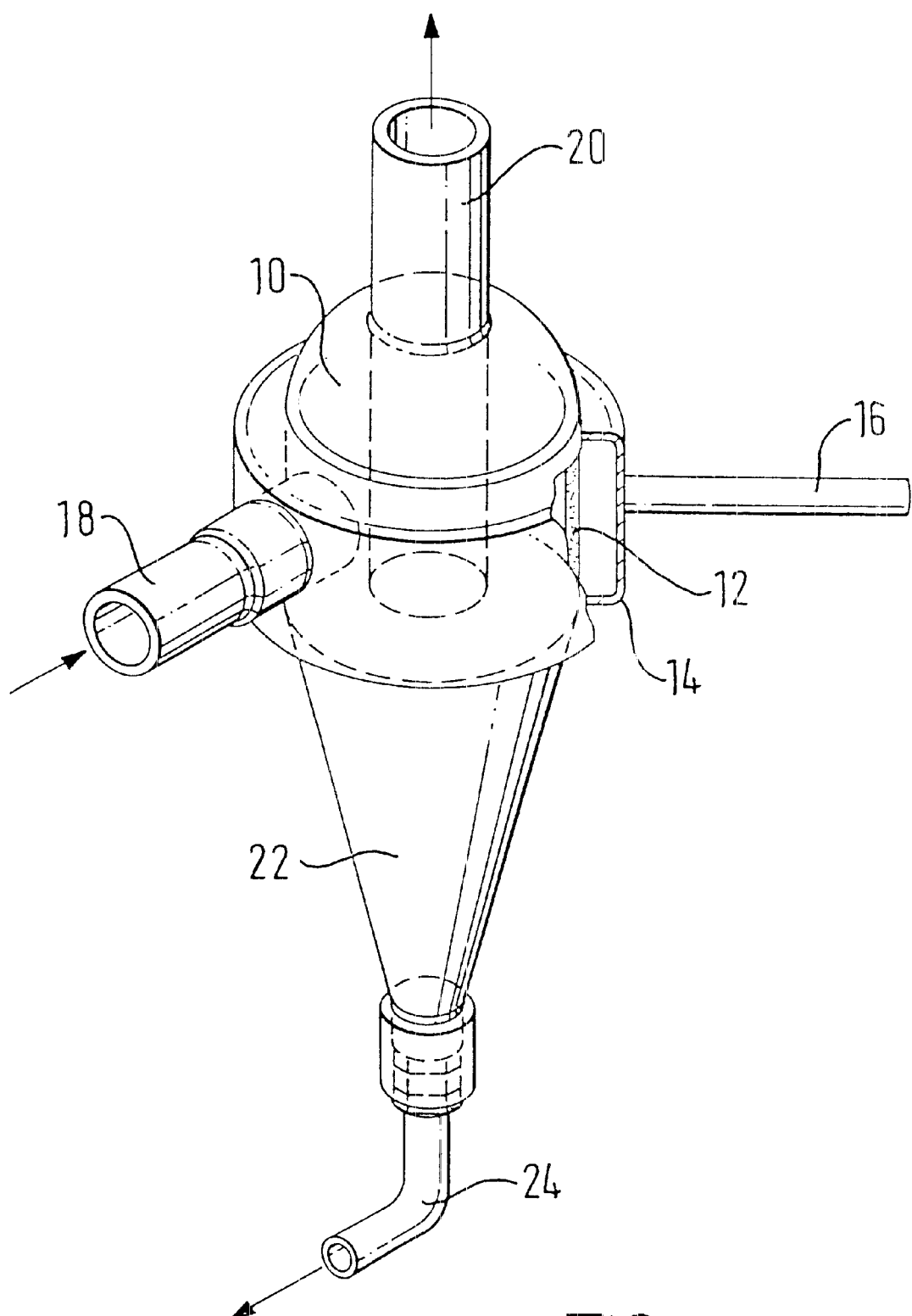
FIG. 1 illustrates a cyclone separator in accordance with the invention.
Figure 2:
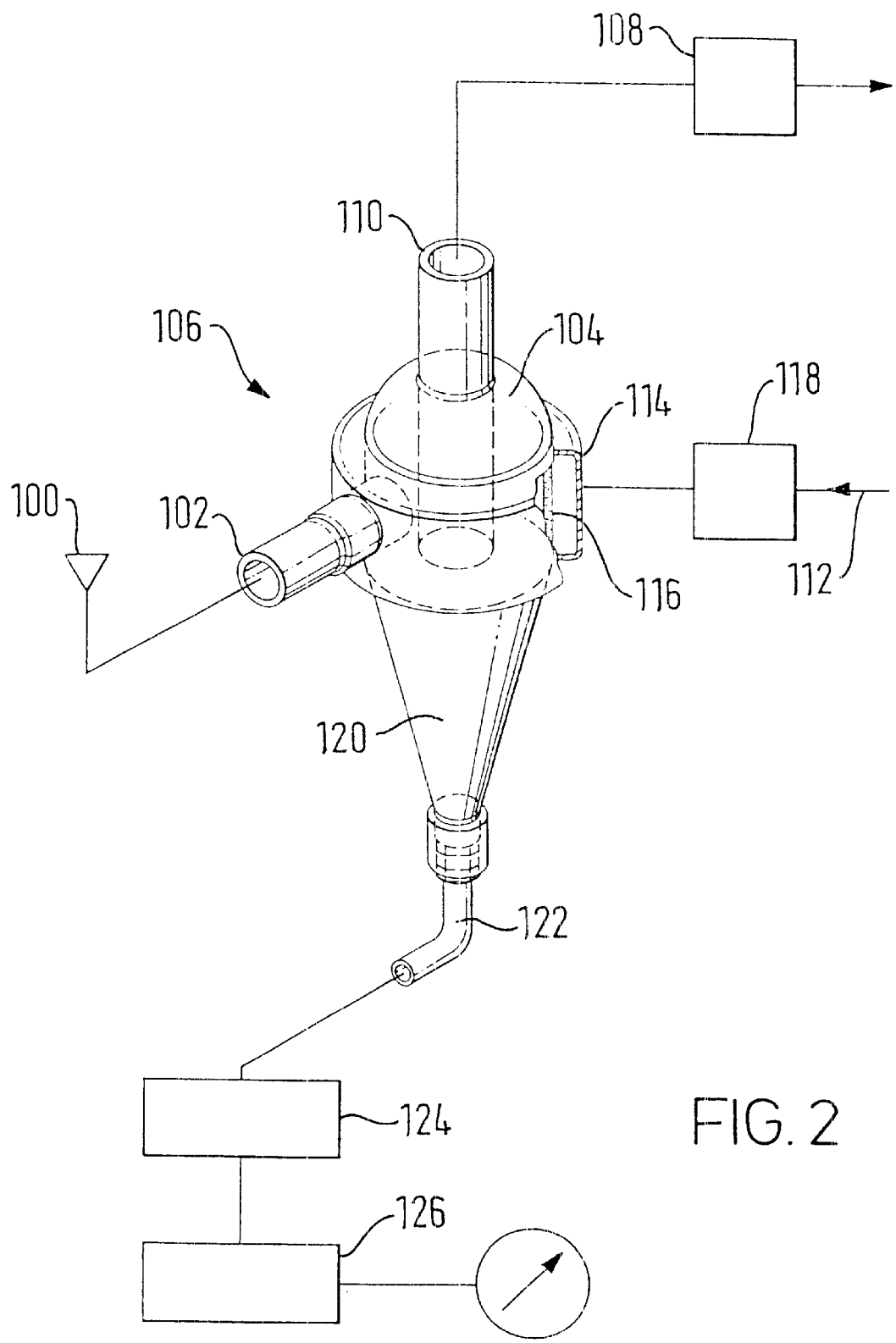
FIG. 2 illustrates, diagrammatically, an instrument for collecting, separating and analysing air borne materials, the instrument comprising a cyclone separator such as shown in FIG. 1.

Referring to FIG. 1, a wetted-wall cyclone separator in accordance with the invention comprises a cylindrical separator chamber 10, provided with a side wall 12, of porous material, itself surrounded by a sealed chamber 14, forming a water jacket about wall 12. The sealed chamber 14 is provided with a pipe 16 for the introduction into sealed chamber 14 of water under pressure.

Air inlet 18 is provided for the introduction of sampled air, for example ambient atmospheric air, to the cylindrical separator chamber 10, which is also provided with a central axial exhaust air outlet 20.

The lower part of cylindrical separator chamber 10 sits upon a tapered conical collection zone 22, terminated by a collector pipe 24 through which the wall washing water and any collected particulates are removed from the separator.

In use, sampled air, which may carry particulates of interest, is introduced, by means of differential pressure, into the cylindrical separator chamber 10, through air inlet pipe 18.

Water under pressure, introduced into water jacket 14, through water pipe 16, is forced through the porous wall 12 of the cylindrical separator chamber 10 to provide a continuous uniform film of water over the inner surface of porous wall 12 of chamber 10.

Particulates entrained in the air incoming through inlet 18 are centrifuged to the wall 12 of separator chamber 10, and are there entrapped in the continuous water film introduced under pressure through porous wall 12 and flowing across its inner surface, and flow with the water into collection zone 22 and out through collector pipe 24, for collection, and, if required, separation and analysis.

A suitable material for the porous wall 12 of separator chamber 10 is, for example, sintered stainless steel, although other suitably porous and inert materials such as ceramics may also be employed.

By surrounding the porous wall 12 with a sealed jacket 14, water introduced through inlet 16 under pressure is forced through the porous wall 12. If the pressure acting upon the water in the jacket 14 is maintained sensibly constant thoughout, and the porous wall 12 is of a controlled porosity, a continuous film of water will form on the inner surface of porous wall 12, entrapping and collecting centrifuged particles from the incoming air stream, wherever the particles may happen to fall upon the inner surface of the separator chamber wall 12.

Relative to the prior art inlet-spray cyclone separator, a cyclone wetted-wall separator in accordance with the present invention system offers improved sample collection efficiency due to the substantially uniform and continuous water film flowing across the inner face of the separator chamber wall 12.

A further advantage of a cyclone separator in accordance with the present invention is that the volume of liquid lost to the airstream through evaporation, and as water droplets, is greatly reduced relative to the losses incurred in an inlet-spray separator.

A still further advantage offered by a cyclone wetted-wall separator in accordance with the invention is that where operation is at temperatures that would be expected to to freeze the collecting liquid, less energy, relative to an inlet-spray separator, is needed to prevent the collecting liquid from freezing, as only the cyclone wall, the water jacket, or the water supply, need to be heated, rather than the whole assembly and incoming analyte-bearing air or other gas in the case of an inlet spray separator.

Such an energy saving is particularly valuable in the case of portable instruments operated from a portable source of electrical energy such as a storage battery.

FIG. 2 illustrates, diagramatically, an airborne particulate collection and analysis instrument incorporating a wetted-wall cyclone separator of the type described with reference to FIG. 1.

Ambient air, together with any airborne analyte in the form of particulate material or vapour, is sampled by means of air sampler 100 and conveyed through air inlet 102 to the separator chamber 104 of wetted wall cyclone separator 106. Air flow into and through separator 106 is produced by air pump 108 attached to air outlet 110 of the cyclone separator chamber 104.

Water from line 112 is pumped into the sealed water chamber 114 surrounding the porous wall 116 of the separator chamber 104 by means of pump 118, and after passing through porous wall 116 produces a continuous uniform film over the inner surface of the porous wall 116.

Cyclonic action of incoming air is induced by the exhaust pump 108, and any airborne particulates or vapours are deposited upon the inner surface of porous wall 116 and entrained in the continuous water film flowing thereover.

The water and entrained analyte flow under the action of gravity to the adjoining collection zone 120 and through collector pipe 122 to sample treatment means 124 and sample detection means 126.

The nature of the sample treatment means 124 and the sample detection means 126, generally known in the art, will be determined by the nature of the analyte materials of interest.

Whilst specific examples of a separator and an instrument incorporating a separator in accordance with the invention have been described, it will be apparent that modifications may be made thereto without exceeding the scope of the invention.

For example whilst the invention has been described in terms of the collection of airborne particulate materials, airborne vapours may be similarly collected and entrained in the water film flowing across the surface of the porous wall of the separator and conveyed to appropriate sample treatment and analysis means.

Similarly although the wall coating and sample collecting liquid in the embodiments described is water, other liquids appropriate to the application may be employed. These may be aqueous solutions or any other liquid(s) compatible with the analyte, the analyte treatment means and any detector employed.

Under certain conditions, a cyclone separator in accordance with the invention may be provided with an inlet spray devices in which the incoming analyte-bearing air or gas stream has a liquid, such as water, sprayed into it.

What is claimed is:

1. A cyclone separator for the separation of particulate materials from a particle-bearing gas or vapour, the separator comprising a separator chamber defined by a porous cylindrical wall through which a liquid is passed to from a film on an inner surface thereof, whereby the film collects particles from said gas or vapour when tangentially introduced into said chamber, the liquid and collected particles falling to the bottom of the chamber.

2. A cyclone separator as claimed in claim 1 in which the porous part of the separating chamber wall is a sintered material.

3. A cyclone separator as claimed in claim 2 in which the sintered material is a ceramic.

4. A cyclone separator as claimed in claim 2 in which the sintered material is a metal.

5. A cyclone separator as claimed in claim 4 in which the metal is stainless steel.

6. A cyclone separator as claimed in claim 1 in which the liquid is water.

7. A cyclone separator as claimed in claim 1 in which the liquid is an aqueous solution.

8. A cyclone separator as claimed in claim 1 further including inlet spray means enabling a liquid to be sprayed into the incoming material-bearing gas or vapour prior to separation in the separating chamber.

9. A cyclone separator as claimed in claim 8 in which the liquid is water.

10. A method of separating a gas or vapour-borne material by means of a cyclone separator in which at least part of the inner wall of the separating chamber of the cyclone separator is cylindrical and porous, the wall being wetted by means of liquid incoming through the porous part, the separated material being collected and carried away by the flow of the liquid over the inner wall of the chamber.

11. A cyclone separator for the separation of gaseous materials from a material-bearing gas or vapour, the separator comprising a separating chamber defined by a porous cylindrical wall through which a liquid is passed to form a film on an inner surface thereof, whereby the film collects particles from said gas or vapour when tangentially introduced into said chamber, the liquid and collected particles falling to the bottom of the chamber.

12. A cyclone separator as claimed in claim 11 further provided with inlet spray means enabling a liquid to be sprayed into the incoming material-bearing gas or vapour prior to separation in the separating chamber.

13. A cyclone separator in accordance with claim 12 in which the liquid is water.

14. A cyclone separator for the separation of vapourous materials from a material-bearing gas or vapour, the separator comprising a separating chamber defined by a porous cylindrical wall through which a liquid is passed to form a film on an inner surface thereof, whereby the film collects particles from said gas or vapour when tangentially introduced into said chamber, the liquid and collected particles falling to the bottom of the chamber.

15. A cyclone separator as claimed in claim 14 further provided with inlet spray means enabling a liquid to be sprayed into the incoming material-bearing gas or vapour prior to separation in the separating chamber.

16. A cyclone separator in accordance with claim 15 in which the liquid is water.

17. A method of separating particles from a particle-bearing gas or vapour comprising the steps of:
   a) injecting the particle-bearing gas or vapour into a separating chamber of a cyclone separator;
   b) centrifuging the particles to a separating chamber wall in which at least part of an inner wall of the separating chamber of the cyclone separator is cylindrical and porous such that the centrifuged particles fall to a bottom of the separating chamber for collection; and,
   c) wetting the chamber wall with a liquid being transmitted through the porous part in order to assist in the collection of the centrifuged particles from the separating chamber wall so that the centrifuged particles may be carried away by the flow of the liquid over the inner wall of the chamber.

18. A method of separating gaseous materials from a material-bearing gas or vapour comprising the steps of:
   a) injecting the material-bearing gas or vapour into a separating chamber of a cyclone separator;
   b) centrifuging the gaseous materials to a separating chamber wall in which at least part of an inner wall of the separating chamber of the cyclone separator is cylindrical and porous such that the centrifuged gaseous materials fall to a bottom of the separating chamber for collection; and,
   c) wetting the chamber wall with a liquid being transmitted through the porous part in order to assist in the collection of the centrifuged gaseous materials from the separating chamber wall so that the centrifuged gaseous materials may be carried away by the flow of the liquid over the inner wall of the chamber.

19. A method of separating vapourous materials from a material-bearing gas or vapour comprising the steps of:
   a) injecting the material-bearing gas or vapour into a separating chamber of a cyclone separator;
   b) centrifuging the vapourous materials to a separating chamber wall in which at least part of an inner wall of the separating chamber of the cyclone separator is cylindrical and porous such that the centrifuged vapourous materials fall to a bottom of the separating chamber for collection; and,
   c) wetting the chamber wall with a liquid being transmitted through the porous part in order to assist in the collection of the centrifuged vapourous materials from the separating chamber wall so that the centrifuged vapourous materials may be carried away by the flow of the liquid over the inner wall of the chamber.

20. A method of separating particles from a particle-bearing gas or vapour, comprising the steps of:
   a. tangentially introducing a particle-bearing gas or vapour into a separating chamber defined by a porous cylindrical wall;
   b. passing a liquid through the wall to form a film on an inner surface thereof; and
   c. allowing particles to be collected by the film and allowing the liquid and collected particles to fall to the bottom of the chamber.

21. A method of separating gaseous materials from a material-bearing gas or vapour comprising the steps of:
   a. tangentially introducing a material-bearing gas or vapour into a separating chamber defined by a porous cylindrical wall;
   b. passing a liquid through the wall to form a film on an inner surface thereof; and
   c. allowing gaseous materials to be collected by the film and allowing the liquid and collected gaseous materials to fall to the bottom of the chamber.

22. A method of separating vapourous materials from a material-bearing gas or vapour comprising the steps of:
   a. tangentially introducing a material-bearing gas or vapour into a separating chamber defined by a porous cylindrical wall;
   b. passing a liquid through the wall to form a film on an inner surface thereof; and
   c. allowing vapourous materials to be collected by the film and allowing the liquid and collected vapourous materials to fall to the bottom of the chamber.

* * * * *